(12) United States Patent
Al Dandachi Atassi

(10) Patent No.: US 8,404,748 B2
(45) Date of Patent: Mar. 26, 2013

(54) STORAGE-STABLE FORMULATION OF PARACETAMOL IN AQUEOUS SOLUTION

(75) Inventor: Khaled Al Dandachi Atassi, Brussels (BE)

(73) Assignee: Neogen N.V., Diegem (BE)

( * ) Notice: Subject to any disclaimer, the term of this patent is extended or adjusted under 35 U.S.C. 154(b) by 2 days.

(21) Appl. No.: 12/797,478

(22) Filed: Jun. 9, 2010

(65) Prior Publication Data

US 2011/0039938 A1    Feb. 17, 2011

Related U.S. Application Data

(63) Continuation of application No. PCT/EP2009/060478, filed on Aug. 13, 2009.

(51) Int. Cl.
*A61K 31/67* (2006.01)
*A61P 29/00* (2006.01)

(52) U.S. Cl. ................................................ 514/629

(58) Field of Classification Search ............... 514/629
See application file for complete search history.

(56) References Cited

U.S. PATENT DOCUMENTS

| | | | |
|---|---|---|---|
| 6,028,222 A | 2/2000 | Dietlin et al. | |
| 6,992,218 B2 * | 1/2006 | Dietlin et al. | ............ 564/4 |

FOREIGN PATENT DOCUMENTS

| | | |
|---|---|---|
| DE | 279 405 | 6/1990 |
| EP | 0 916 347 | 2/2003 |
| EP | 1 889 607 | 2/2008 |
| EP | 1 992 334 | 11/2008 |
| GR | 871510 | 9/1987 |
| GR | 1001523 | 1/1994 |
| GR | 1002731 | 4/1997 |
| WO | WO 02/072080 | 9/2002 |
| WO | WO 2008/135601 | 11/2008 |
| WO | WO 2009/081283 | 7/2009 |

OTHER PUBLICATIONS

Perfalgan® Consumer Medicine Information leaflet, Jul. 2004, 2 pages.
Shug, Update on Acute Pain Service 2006. downloaded from http://www.rph.wa.gov.au/anaesth/downloads/APS%20Update%202006.pdf, Feb. 10, 2011, 49 pages.
International Search Report issued May 11, 2010 to international application No. PCT/EP2009/060478.
Cadence Pharmaceuticals, 2011 Annual Report, May 4, 2012, 116 pages.

\* cited by examiner

*Primary Examiner* — San-Ming Hui
*Assistant Examiner* — Kathrien Cruz
(74) *Attorney, Agent, or Firm* — Knobbe, Martens, Olson & Bear LLP

(57) ABSTRACT

The present invention concerns a liquid formulation that is stable to oxidation and that is based on paracetamol in an aqueous solvent obtainable by the following steps: (i) dissolving in a reaction vessel paracetamol in an aqueous solvent having a temperature between 65° C. and 95° C., and having pH between 5.0 and 6.0; (ii) cooling the solution so formed to a temperature equal to or above 35° C. and below 40° C. under an atmosphere of nitrogen; (iii) adding cysteine hydrochloride and sodium hydroxide simultaneously to the solution without stirring; (iv) closing the reaction vessel, and stirring the solution of step iii) in a nitrogen atmosphere. It further relates to a method for preparing the formulation.

17 Claims, No Drawings

STORAGE-STABLE FORMULATION OF PARACETAMOL IN AQUEOUS SOLUTION

RELATED APPLICATIONS

This application is a continuation of PCT Application No. PCT/EP2009/060478, filed Aug. 13, 2009, which is incorporated herein by reference.

BACKGROUND OF THE INVENTION

1. Field of the Invention

The object of the present invention is a new formulation and a new method for producing injectable aqueous solutions containing paracetamol, and a procedure for preparation of these methods of packaging, and their utilization.

2. Description of the Related Art

Paracetamol (INN of acetaminophen or N-(4-hydroxyphenyl)acetamide) is an analgesic and an antipyretic widely used in hospitals. It is desirable to have available stable liquid pharmaceutical formulations of this active principle for administration by injection, in particular for intravenous infusion.

It is known that paracetamol in aqueous solution is liable to undergo hydrolysis to form p-aminophenol, which is itself liable to degrade into quinoneimine (cf. for example J. E. Fairbrother, "Acetaminophen" in Analytical Profiles of Drug Substances, 1974, vol. 3, pp. 1-109). The rate of degradation of paracetamol increases with increasing temperature and light. This rate is minimal at a pH in the region of 6 (K. T. Koshy et al., 1961, J. Pharm. Sci. 50, pp. 116-118).

It is known practice to add a buffer and an antioxidant or free-radical scavenger to stabilize paracetamol in solution.

WO 02/072 080, for example, describes stable aqueous paracetamol solutions for infusion comprising a buffer of pH 5.5 to 6.5 and an antioxidant chosen from ascorbic acid and a derivative bearing a thiol function.

EP 0 916 347 discloses-paracetamol solutions based on a mixture of water and of alcoholic solvents comprising a buffer of pH 5.5 to 5.6 and metabisulfite as antioxidant.

EP 0 859 329 describes a deoxygenation process by which the aqueous solvent is deoxygenated by bubbling into an inert gas, such as nitrogen.

Also US 2004/0054012 describes a deoxygenation process involving the bubbling of an inert gas such as nitrogen through the aqueous solution.

WO 2008/135601 describes aqueous paracetamol solutions for infusion prepared using high temperatures and in an oxygen-free environment.

Some of the prior-art stabilized injectable solutions of paracetamol have the drawback of requiring the total absence of oxygen during the production process. However, oxygen shows a very great facility to dissolve in water, making it necessary to ensure that the solution, once deoxygenated, does not subsequently come into contact with atmospheric air at every stage in the production process. The methods of the art, therefore, require a considerable amount of time, care, and the use of specialised equipment and/or protocols. Even with all these precautions, total absence of oxygen can never be ensured during all the preparatory steps. In presence of even traces of oxygen, degradation products can be generated which increase in quantity during storage of the product, and ultimately leads to a reduced shelf-life.

The main object of the present invention is to provide a formulation and a method for aqueous formulations of paracetamol, which can notably be utilized in injectable preparations being stable over a long period, which solves the problems in view of the problems of the art.

SUMMARY OF SOME EMBODIMENTS OF THE INVENTION

One embodiment of the invention is a liquid formulation that is stable to oxidation and that is based on paracetamol in an aqueous solvent obtainable by the following steps:
i) dissolving in a reaction vessel paracetamol in an aqueous solvent having a temperature between 65° C. and 95° C., and having pH between 5.0 and 6.0
ii) cooling the solution so formed to a temperature equal to or above 35° C. and below 40° C. under an atmosphere of nitrogen,
iii) adding cysteine hydrochloride and sodium hydroxide simultaneously to the solution without stirring,
iv) closing the reaction vessel, and stirring the solution of step iii) in a nitrogen atmosphere.

Another embodiment of the invention is a liquid formulation as described above, wherein the aqueous solvent has a temperature between 70° C. and 90° and preferably between 75° C. and 85° C.

Another embodiment of the invention is a liquid formulation as described above, wherein the aqueous solvent has a pH between 5.6 and 5.7, and preferably of 5.5.

Another embodiment of the invention is a liquid formulation as described above, wherein the aqueous solvent comprises water, an isotonic agent and a buffer agent.

Another embodiment of the invention is a liquid formulation as described above, wherein the isotonic agent is a polyol, a sugar, a linear or cyclic glucitol having from 2 to 10 carbon atoms selected from mannitol, sorbitol, inositol, glucose and glycerol, and preferably mannitol.

Another embodiment of the invention is a liquid formulation as described above, wherein the mass ratio of mannitol: paracetamol is between 2 to 6:1, preferably 3 to 5:1, preferably 4:1.

Another embodiment of the invention is a liquid formulation as described above, wherein the sodium hydroxide is added in step iii) to a final pH of between 5.6 and 5.8, and preferably around 5.7.

Another embodiment of the invention is a liquid formulation as described above, wherein the paracetamol is present in an amount of between 0.25 and 2% (w/v).

Another embodiment of the invention is a liquid formulation as described above, wherein the solution in step iv) is subsequently filtered in a filtration unit prior to packaging in one or more vials.

Another embodiment of the invention is a method for the production of a formulation as described above, comprising the steps of:
i) dissolving paracetamol in an aqueous solvent having a temperature between 65° C. and 95° C., and having pH between 5.0 and 6.0 in a reaction vessel
ii) replacing the remaining air in the vessel by an inert gas, such as nitrogen, and cooling the solution so formed to a temperature equal to or above 35° C. and below 40° C.,
iii) adding cysteine hydrochloride and sodium hydroxide simultaneously to the solution without stirring, and
iv) closing the reaction vessel and stirring the solution of step iii) in a nitrogen atmosphere.

Another embodiment of the invention is a method as described, further limited by the features of of the formulation cited above.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

Throughout this application, the term "about" is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of items, and can also include 1.5, 2, 2.75 and 3.80, when referring to, for example, concentrations). The recitation of end points also includes the end point values themselves (e.g. from 1.0 to 5.0 includes both 1.0 and 5.0)

The invention provides in a first aspect a liquid formulation that is stable to oxidation and that is based on paracetamol in an aqueous solvent. The formulation is characterized in that the paracetamol is admixed in the aqueous solvent having, as from the outset, a temperature between 65° C. and 95° C. The pH of the aqueous solvent is between 5.0 and 6.0. Under a nitrogen atmosphere, the solution is subsequently cooled to a temperature equal to or above 35° C., and below 40° C., after which cysteine hydrochloride and sodium hydroxide are simultaneously added without stirring. The addition is preferably rapid. The mixture is subsequently stirred in an atmosphere of nitrogen to yield a formulation of the invention.

Therefore, the invention provides in a first aspect a liquid formulation that is stable to oxidation and that is based on paracetamol in an aqueous solvent obtainable by the following steps:
i) dissolving in a reaction vessel paracetamol in an aqueous solvent having a temperature between 65° C. and 95° C., and having pH between 5.0 and 6.0,
ii) cooling the solution so formed to a temperature equal to or above 35° C., and below 40° C. under an atmosphere of nitrogen,
iii) adding cysteine hydrochloride and sodium hydroxide simultaneously to the solution without stirring, and
iv) closing the reaction vessel, and stirring the solution of step iii) in a nitrogen atmosphere.

In a second aspect, the invention relates to a method for the production of a formulation as defined herein, comprising the steps of:
i) dissolving paracetamol in an aqueous solvent having a temperature between 65° C. and 95° C., and having pH between 5.0 and 6.0 in a reaction vessel,
ii) replacing the remaining air in the vessel by an inert gas, such as nitrogen, and cooling the solution so formed to a temperature below 40° C.,
iii) adding cysteine hydrochloride and sodium hydroxide simultaneously to the solution without stirring, and
iv) closing the reaction vessel, and stirring the solution of step iii) in a nitrogen atmosphere.

The invention also relates to a liquid formulation obtainable by the method of the invention.

As such, this method according to the present invention for the production of a formulation as defined herein involves the use of an aqueous solvent which is characterized by a high temperature (between 65° C. and 95° C.) as from the outset, a cooling step (to below 40° C.), and the addition of cysteine hydrochloride and sodium hydroxide. The cysteine hydrochloride and sodium hydroxide are added without mechanical agitation such as stirring. They are preferably added rapidly.

The sodium hydroxide is added to ensure a final pH of between 5.6 and 5.8, and preferably around 5.7.

In an embodiment, the invention relates to a formulation and method as defined herein, wherein the aqueous solvent has, as from the outset, a temperature between 65° C. and 95° or between 70° C. and 90° or between 75° C. and 85° C.

In another embodiment, the invention relates to a formulation and method as defined herein, wherein the aqueous solvent has a pH between 5.0 and 6.0, 5.6 and 5.7 and preferably around 5.5. The pH may be adjusted prior to admixing using NaOH or HCl.

In an embodiment, the invention relates to a formulation and method as defined herein, wherein the paracetamol solution so formed is cooled to a temperature of less than 40° C., preferably equal to or above 35° C. and below 40° C., between 35° C. and 39° C. or between 36° C. and 38° C. or at 37° C. Preferably, the cooling (step (ii)) may be under mechanical agitation e.g. stirring.

In yet another embodiment, the invention relates to a formulation and method as defined herein, wherein the aqueous solvent comprises water, an isotonic agent and a buffer agent.

The invention further provides a formulation and method as defined herein wherein the solution of step iv), is subsequently filtered. The filtering may take place at a temperature of less than 40° C., preferably equal to or above 35° C. and below 40° C., between 35° C. and 39° C. or between 36° C. and 38° C. or between 37° C.

The invention further provides a formulation and method as defined herein wherein the paracetamol is present in the final formulation in an amount of (w/v) of 0.25%, 0.5%, 1%, 1.5%, 2%, 2.5%, 3%, or a value in the range between any two of the aforementioned values, preferably between 0.25 and 2%, preferably around 1%. Preferably, the paracetamol is dissolved in the aqueous solvent (step (i)) under mechanical agitation e.g. stirring.

For the purpose of improving the stability of a liquid formulation of paracetamol, and thus to overcome the disadvantages described above, the present invention provides a method and a formulation which avoids minimising the oxygen in the aqueous solvent as from the outset, and oxygen is eliminated or reduced by temperature-controlled manufacturing wherein the temperature is initially set at and maintained within 65° C. and 95° C. before cooling to a temperature of less than 40° C., preferably equal to or above 35° C. and below 40° C., and cysteine hydrochloride and sodium hydroxide are added after the second cooling step. The invention therefore provides in a first aspect a liquid, stable to oxidation formulation based on paracetamol, while being able to be preserved for a prolonged period, characterized in that the paracetamol is admixed in the aqueous solvent having a temperature between 65° C. and 95° C. and having a pH between 5.0 and 6.0, the solution is cooled to a temperature of less than 40° C., preferably equal to or above 35° C. and below 40° C., and cysteine hydrochloride and sodium hydroxide are added.

It is not essential to purge the aqueous solvent with nitrogen as from the outset. Air in the reaction vessel is replaced with nitrogen after the addition of paracetamol and after the addition of cysteine hydrochloride/sodium hydroxide. The nitrogen is preferably put under pressure. Eventually, the filling and packaging of the vials can also take place with the addition of an inert gas, such as nitrogen.

The invention relates to a formulation and method as defined herein, wherein the aqueous solvent comprises water, an isotonic agent and a buffer agent. The aqueous solvent may or may not have a low concentration of dissolved oxygen i.e. there is no requirement to purge the aqueous solution with an inert gas such as nitrogen.

A formulation according to the present invention contains a buffer agent with a pKa of between 4.5 and 6.5 and preferably between 5.0 and 6.2. This buffer agent will advantageously be chosen from citrate buffer, phosphate buffer, phosphate-citrate buffer, bicarbonate buffer, tartrate buffer and acetate buffer, preferably from citrate buffer, phosphate buffer and phosphate-citrate buffer, or a mixture of these buffers. Most preferably, the buffer agent is disodium phosphate dihydrate ($Na_2HPO_4 2H_2O$). The mass ratio (w/w) of the buffer agent:paracetamol, for instance $Na_2HPO_4 2H_2O$:paracetamol is preferably 0.005 to 0.025:1, preferably 0.010 to 0.020:1, preferably 0.015:1.

The present formulations for injection further contain an isotonic agent, intended to create an osmotic pressure in the region of that of physiological saline. The isotonic agent also referred to as isotonic agent herein may be a polyol, a sugar, a linear or cyclic glucitol having from 2 to 10 carbon atoms selected from mannitol, sorbitol, inositol, glucose and glycerol. This isotonic agent can be chosen from sodium chloride and glucose. A preferred isotonic agent is mannitol. The mass ratio (w/w) of the isotonic agent:paracetamol, for instance mannitol:paracetamol is preferably 2 to 6:1, preferably 3 to 5:1, preferably 4:1.

Cysteine hydrochloride and sodium hydroxide are added to the paracetamol solution under the conditions described to act as an anti-oxidising agent. The cysteine hydrochloride is preferably the monohydrate. By adding the cysteine hydrochloride with sodium hydroxide, the final pH of the formulation is between 5.6 and 5.8. The cysteine hydrochloride and sodium hydroxide are added immediately after the solution has cooled to between 35° C. and 39° C. The cysteine hydrochloride and sodium hydroxide are added without mechanical agitation such as stirring to prevent entry of oxygen into the solution. After addition, the reaction vessel is closed, put under a nitrogen atmosphere, stirring ensues, and the solution maintained at a temperature between 40° C., preferably equal to or above 35° C. and below 40° C., between 35° C. and 39° C. or between 36° C. and 38° C. or between 37° C. The mass ratio (w/w) of cysteine hydrochloride:paracetamol is 0.010 to 0.040:1, preferably 0.020 to 0.030:1, preferably 0.025:1

The formulation of the invention is generally prepared as follows. First an aqueous solvent or solution is prepared by mixing together water suitable for injection (WFI), a buffer and an isotonic agent, at a pH from 5 to 6 and preferably at a pH of about 5.5. The pH can be adjusted by q.s. (sufficient quantity) of NaOH or HCl. Optionally one or more other water-miscible solvent(s), and/or surfactants might be present. Then, in a reaction vessel, paracetamol is admixed to the aqueous solvent, the solvent being provided at a temperature of between 65° C. and 95° C. After paracetamol addition and mixing, air in the reaction vessel is substituted by nitrogen and put under nitrogen pressure. The solution is cooled to a temperature of less than 40° C., preferably equal to or above 35° C. and below 40° C., between 35° C. and 39° C. or between 36° C. and 38° C. or between 37° C. Once cooled, cysteine hydrochloride monohydrate and sodium hydroxide are added together without stirring. The reaction vessel is closed, put under an atmosphere of nitrogen using filtered nitrogen gas (preferably filtered with a 0.22 µm filter) and stirring is performed. The NaOH is added so as to ensure a pH of between 5.6 and 5.8.

The invention also relates to a formulation as defined above that may be obtained via this process.

After stirring the solution in step iv), the obtained solution may be filtered in a filtration unit. The subsequent filtration of the obtained mixture preferably takes place between 35° C. and 39° C. Precautions may be taken for this purpose to replace the air in the filtration unit with an inert gas such as nitrogen, which gas will eventually be applied under pressure in the filtration unit to drive the solution across the filtration membrane. Eventually, the filling and packaging of the vials can also take place with the addition of an inert gas, such as nitrogen. These bottles can be subsequently sterilised for 15 minutes at 121° C.

An important advantage of the present process comprises admixing of the paracetamol to the aqueous solvent that has a temperature of between 65° C. and 95° C., cooling the solution so formed to a temperature below 40° C., preferably equal to or above 35° C. and below 40° C., and adding cysteine hydrochloride and NaOH. There is no requirement to purge the aqueous solution of oxygen using, for example, nitrogen gas. Indeed, total absence of oxygen can never be ensured during all the preparatory steps such as filtration of the solution, and during filling into the vials. In presence of even traces of oxygen, two kinds of degradation products that can be generated:

due to heat action during sterilisation, a dimer of paracetamol may be formed. This dimer is a degradation product. This dimer is also significantly increased during storage of the product.

other unknown degradation products of paracetamol by oxidation are also generated during storage of the product.

Owing to the combination of steps, notably the temperature, cooling and cysteine, dimer formation is avoided during sterilisation, and increase of its level during storage is also avoided. Thereby, the shelf-life of the product is increased.

Cysteine hydrochloride as anti-oxidant avoids the generation of the unknown degradation product of paracetamol by oxidation. It is added at a temperature of between 35° C. and 39° C. to avoid degradation of the cysteine hydrochloride at higher temperatures.

The invention is described in greater detail in the examples below, which are given as non-limiting illustrations. In these examples, the temperature is room temperature or is expressed in degrees Celsius, and the pressure is atmospheric pressure. The water and all the reagents used are of injectable grade.

Moreover, all the examples form an integral part of the invention, as does any characteristic of the description including the examples, which appears to be novel with respect to any prior art, in the form of a general characteristic rather than of a particular characteristic of the example.

EXAMPLES

1. Preparation of Liquid Pharmaceutical Formulations According to the Invention

Formulations were prepared by admixing paracetamol to a solution of water for injection, buffer (phosphate buffer) and isotonic agent (mannitol), filtration and filling of glass vials or bottles. These bottles can then be sterilized for 15 minutes at 121° C.

Formulation 1

| Name of ingredient | Unit formula 100 ml | Formula per 1 ml |
| --- | --- | --- |
| Paracetamol | 1.0 g | 10 mg |
| Mannitol | 3.9096 g | 39.096 mg |
| Di sodium Phosphate dihydrate | 15.0 mg | 0.15 mg |
| Hydrochloric acid | to pH = 5.5 | to pH = 5.5 |
| Cysteine hydrochloride monohydrate | 25.0 mg | 0.25 mg |
| Sodium hydroxide | 0.14 ml | 0.0014 ml |
| Water For Injection | q.s. ad 100.0 ml | q.s. ad 1.0 ml |
| Nitrogen Low Oxygen | q.s. | q.s. |

The required tubes and filters are usually pre-sterilized at high temperatures and may be readily used at the above-mentioned temperature. The relevant manufacturing steps are performed quickly and without any unnecessary interruption in order to avoid contact of the solution with air and to keep the solution at the required temperatures e.g. between 65° C. and 95° C. for step i) and equal to or above 35° C. and below 40° C. for step ii).

In a first step (comprising step i) a reaction vessel equipped with a stirrer is provided with about 90% of the total required quantity WFI (water for injection), which under some circumstances and preferably can be taken directly from a WFI loop at temperature between 75° C. and 85° C. The weights are registered. Then the following steps are performed: add smoothly and without stirring the required amount of isotonic agent, preferably mannitol and the buffer, preferably disodium phosphate dehydrate. Stir the obtained mixture until complete dissolution (normally about 1 to 2 minutes). Reopen the vessel and measure and adjust the pH. Provide, therefore, within the vessel a special electrode for pH measurement at temperature between 80° C. and 100° C. and under minimum speed stirring, adjust the pH to 5.5 with e.g. HCl or NaOH 0.1N. Once the pH has been set at about 5.5, and preferably at 5.5, stop stirring the solution and add the required amount of paracetamol. Stir the obtained mixture until complete dissolution of paracetamol (about 1 minute) and bring quickly to final volume with WFI between 75° C. and 85° C. taking into consideration the density thereof Stir for about 1 minute. Check the pH. Adjust to pH 5.5 with HCL 0.1N or NaOH 0.1N if necessary.

In a second step (step ii), the vessel is put under (0.22 μm filtered) nitrogen pressure and closed, while the temperature is dropped to between 35° C. and 39° C. The temperature drop is preferably achieved by applying no or less heat, rather than using a cooling agent.

In a third step (step iii), the vessel is opened and the appropriate quantities of cysteine hydrochloride monohydrate and sodium hydroxide are added. The vessel is closed, and stirring continued in the temperature range between 35° C. and 39° C. under (0.22 μm filtered) nitrogen pressure.

The filtration of the solution takes place at a temperature between 35° C. and 39° C. without cooling of the solution. A 0.22 μm filter with sanitary flange inlet and outlet connections and integral vent and drain valves for immediate installation can be used. The filtration vessel is certified for pressure and equipped with 0.22 μm vent filter and 0.22 μm nitrogen filter. Replace the air inside the filtration vessel by 0.22 μm filtered nitrogen and keep it under nitrogen pressure.

Connect the tube IN to the inlet flange of the filter and connect the other side of the tube to the compounding vessel. Connect the tube OUT to the outlet flange of the filter. Apply nitrogen pressure on the solution in the compounding vessel and discard about 300 ml of the solution by the tube that is connected to the outlet flange of the filter. Purge the filter by the drain valve and repeat this operation until no bubbles are present. Connect the tube OUT to the outlet flange of the filter to the filtration vessel. Apply nitrogen pressure on the solution in the compounding vessel to push the solution throughout the filter and open the valve of the vent filter of the filtration vessel. Achieve the filtration and stop the filtration when about 1 litre of solution is still remaining in the compounding vessel. Close off the valve of the vent filter of the filtration vessels and put it under (0.22 μm filtered) nitrogen pressure. Keep the solution in the filtration vessel until the temperature is about 25-27° C. or at room temperature. In this case, the vessel is kept until the next day. If the filtration vessel is equipped with a jacket, cool the solution and continue the operations. The special purging step in the process is preferred to minimize the risk of oxygenation of the mixture.

During the above-mentioned steps the temperature preferably maintained at at least 35° C.

The filling of the solution was performed using known techniques by replacing the air in vials by (0.22 μm filtered) nitrogen until the nitrogen goes out of the needles of the foiling machine. Fill the solution under nitrogen flushing before and after filling.

Finally, the filled vials can be sterilized at 121° C. for 15 minutes.

What is claimed is:

1. A liquid formulation of paracetamol, comprising:
   paracetamol, at a concentration of 0.25-2% (w/v),
   cysteine hydrochloride, wherein the mass ratio cysteine hydrochloride: paracetamol is 0.02:1 to 0.03:1, and
   aqueous solvent,
   wherein the pH of the formulation is 5-6 and wherein degradation products are avoided during sterilization and storage, whereby stability of the liquid formulation of paracetamol is improved.

2. The formulation according to claim 1, wherein the aqueous solvent comprises water, an isotonic agent and a buffer agent.

3. The formulation according to claim 2, wherein the isotonic agent is a polyol, a sugar, or a linear or cyclic glucitol having from 2 to 10 carbon atoms selected from mannitol, sorbitol, inositol, glucose and glycerol.

4. The formulation according to claim 3, wherein the isotonic agent is mannitol.

5. The formulation according to claim 4 wherein the mass ratio of mannitol:paracetamol is betWeen 2:1 and 6:1.

6. The formulation according to claim 4, wherein the mass ratio of mannitol: paracetamol is between 3:1 and 5:1.

7. The formulation according to claim 4, wherein the mass ratio of mannitol:paracetamol is about 4:1.

8. The formulation according to claim 1, wherein the paracetamol is present in an amount of around 1% (w/v).

9. The formulation according to claim 1, which is packaged in one or more vials.

10. The formulation according to claim 2, wherein the buffer agent is disodium phosphate dihydrate.

11. The formulation according to claim 10, wherein the mass ratio of disodium phosphate dihydrate:paracetamol is about 0.005:1 to 0.025:1.

12. The formulation according to claim 10, wherein the mass ratio of disodium phosphate dihydrate:paracetamol is about 0.010:1 to 0.020:1.

13. The formulation according to claim 10, wherein the mass ratio of disodium phosphate dihydrate:paracetamol is about 0.015:1.

14. The formulation according to claim 2, further comprising sodium hydroxide.

15. The formulation according to claim 1, wherein the pH of the formulation is 5.6-5.8.

16. The formulation according to claim 1, wherein the paracetamol is present in an amount of around 1% (w/v).

17. The formulation according to claim 1, wherein the mass ratio cysteine hydrochloride:paracetamol is 0.025:1.

* * * * *